United States Patent [19]

Suzuki et al.

[11] Patent Number: 4,485,160
[45] Date of Patent: Nov. 27, 1984

[54] ELECTROPHOTOGRAPHIC HYDRAZONE PLATE

[75] Inventors: Tetsumi Suzuki, Isehara; Tetsuo Murayama, Machida; Hitoshi Ono; Shinji Aramaki, both of Yokohama, all of Japan

[73] Assignee: Mitsubishi Chemical Industries Limited, Tokyo, Japan

[21] Appl. No.: 508,904

[22] Filed: Jun. 29, 1983

[30] Foreign Application Priority Data

Jul. 16, 1982 [JP] Japan ................................ 57-124056

[51] Int. Cl.³ .............................................. G03G 5/06
[52] U.S. Cl. ....................................... 430/59; 430/73; 564/251
[58] Field of Search .................... 430/59, 73; 564/251

[56] References Cited

U.S. PATENT DOCUMENTS

| | | | |
|---|---|---|---|
| 3,473,883 | 10/1969 | Mix et al. | 564/251 X |
| 4,150,987 | 4/1979 | Anderson et al. | 430/59 X |
| 4,396,694 | 8/1983 | Nagata et al. | 430/59 X |
| 4,420,548 | 12/1983 | Sakai et al. | 430/59 |
| 4,423,129 | 12/1983 | Takasu et al. | 430/59 |

FOREIGN PATENT DOCUMENTS 57-201235 12/1982 Japan ..................................... 430/59

Primary Examiner—Roland E. Martin
Attorney, Agent, or Firm—Oblon, Fisher, Spivak, McClelland & Maier

[57] ABSTRACT

An electrophotographic plate comprising a photosensitive layer containing a hydrazone compound represented by the general formula:

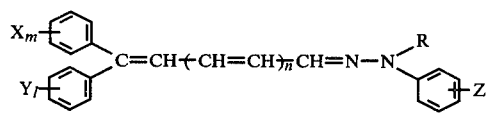

(where X, Y and Z represent independently hydrogen atom, a lower alkyl group, a lower alkoxy group, phenoxy group or an arylalkoxy group; R represents hydrogen atom, a lower alkyl group, allyl group, an aralkyl group or an optionally substituted phenyl group; m and l represent independently 1 or 2; and n represents 0 or 1).

13 Claims, No Drawings

ELECTROPHOTOGRAPHIC HYDRAZONE PLATE

BACKGROUND OF THE INVENTION

1. Field of the Invention

This invention relates to an electrophotographic plate. More particularly, it relates to a highly sensitive electrophotographic plate having a photosensitive layer comprising an organic photoconductive material.

2. Description of the Prior Art

Heretofore, inorganic photoconductive materials such as selenium, cadmium sulfide and zinc oxide have been widely used in the photosensitive layer of the electrophotographic plates. Studies on use of organic photoconductive materials for the photosensitive layer of the electrophotographic plates have been advanced, and some of them have materialized into practical use. The organic photoconductive materials have many advantages over the inorganic materials, for example, they are light in weight, and easy to fabricate as a film, and can be easily manufactured into a photosensitive plate, and into a transparent photosensitive plate depending upon the kinds of the materials. While various studies have been made on the organic photoconductive materials regarding photoconductive polymers represented by polyvinylcarbazole, these polymers are not always satisfactory in view of this film-forming property, flexibility, bondability and the like and they tend to produce cracks or peel off from substrates when formed as a film. Although plasticizer, binder and the like have been added in order to overcome the above-mentioned defects, since such addition is liable to cause another problems such as reduction in the sensitivity and the increase in the residual potential, it has been very difficult to obtain practical photosensitive plates.

On the other hand, while it is easy to prepare photosensitive plates having excellent mechanical properties using low molecular weight-organic photoconductive compounds, since polymers excellent in the film-forming property, flexibility, bondability and the like can be selected as a binder, it has been difficult to find those compounds suitable to the preparation of highly sensitive photosensitive plates.

SUMMARY OF THE INVENTION

In view of the above, the present inventors have made an earnest study on low molecular weight-organic photoconductive compounds capable of providing a highly sensitive and highly durable electrophotographic plate and, as the result, have accomplished this invention based on the finding that a specific hydrazone compound is suitable.

Namely, this invention resides in an electrophotographic plate comprising a photosensitive layer containing a hydrazone compound represented by the general formula (I):

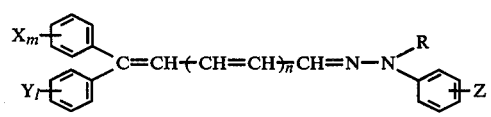
(I)

(wherein X, Y and Z represents independently hydrogen atom, a lower alkyl group, a lower alkoxy group, phenoxy group or an arylalkoxy group; R represents hydrogen atom, a lower alkyl group, allyl group, an aralkyl group or an optionally substituted phenyl group; m and l represent independently 1 or 2; and n represents 0 or 1).

DETAILED DESCRIPTION OF THE PREFERRED EMBODIMENTS

Referring more specifically to this invention, the electrophotographic plate according to this invention contains a hydrazone compound represented by the above general formula (I) in the photosensitive layer.

In the above-mentioned general formula (I), X, Y and Z represent independently hydrogen atom; a lower alkyl group such as methyl, ethyl, propyl, butyl, hexyl or the like; a lower alkoxy group such as methoxy, ethoxy, butoxy or the like; phenoxy; or an arylalkoxy group such as benzyloxy, phenethyloxy or the like.

R represents hydrogen atom; a lower alkyl group such as methyl, ethyl, propyl, butyl, hexyl or the like; allyl; an aralkyl group such as benzyl, phenethyl or the like; or a phenyl group optionally substituted with a group selected from the group consisting of a lower alkyl group such as methyl, ethyl, propyl, butyl, hexyl or the like; a lower alkoxy group such as methoxy, ethoxy, butoxy or the like; phenoxy; or an arylalkoxy group such as benzyloxy, phenethyloxy or the like.

m and l represent independently 1 or 2, and n represents 0 or 1.

Those compounds in which X and Y represent independently a lower alkyl or lower alkoxy group, Z represents hydrogen atom and R represents phenyl in the above general formula (I) are preferred.

The hydrazone compounds represented by the general formula (I) can be produced with ease by known processes.

For example, they can be obtained by reacting acroleins represented by the general formula (II):

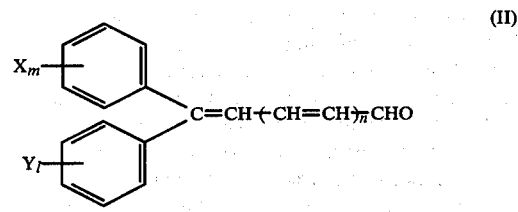
(II)

(where X and Y, l, m and n are as defined here in the general formula (I)), in an organic solvent inert to the reaction, such as benzene, toluene, chlorobenzene, alcohol, acetone, N,N-dimethylformamide, dimethylsulfoxide, tetrahydrofuran, dioxane and the like if required, in the presence of a reaction promotor such as p-toluene sulfonic acid, benzene sulfonic acid, hydrochloric acid, sulfuric acid, potassium acetate, sodium acetate and the like with hydrazines represented by the general formula (III):

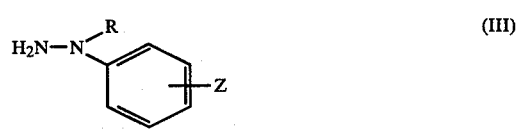
(III)

(wherein R and Z are as defined hereinabove) or hydrochloride or sulfate thereof at the temperature condition of 10°–200° C. and, preferably, 20°–100° C.

Alternately, the hydrazone of the general formula (I) shown above can be produced by reacting an acrolein of the above general formula (II) with a hydrazine represented by the following general formula (IV):

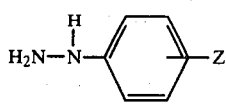  (IV)

(where Z is as defined hereinabove) in an organic solvent inert to the reaction such as benzene, toluene, chlorobenzene, alcohol, acetone, N,N-dimethylformamide, dimethylsulfoxide, tetrahydrofuran, dioxane and the like optionally, under the presence of a reaction promotor such as p-toluene sulfonic acid, benzene sulfonic acid, hydrochloric acid, sulfuric acid, potassium acetate and sodium acetate to produce hydrazones represented by the following general formula (V):

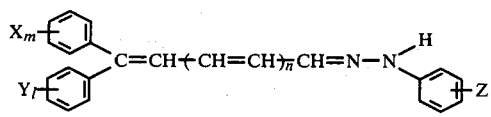  (V)

(where X, Y, Z, m, l and n are as defined in the above general formula (I)) and, thereafter, reacting the same with an alkylating agent, allylating agent, or aralkylating agent represented by the following general formula (VI):

R-W  (VI)

(where R is as defined in the above general formula (I) and W represents halogen atom such as chlorine, bromine or iodine), or dialkyl sulfate such as dimethyl sulfate, diethyl sulfate and the like in an organic solvent inert to the reaction such as tetrahydrofuran, dioxane, N,N-dimethylformamide, N-methylpyrrolidone, dimethylsulfoxide and the like under the coexistence of an acid remover such as sodium hydroxide, potassium hydroxide, sodium carbonate, potassium carbonate, triethylamine, pyridine and trimethylbenzylammonium hydroxide at a temperature between 10°–200° C.

The acroleins as one of the starting materials can be produced, for example, by the following known reaction.

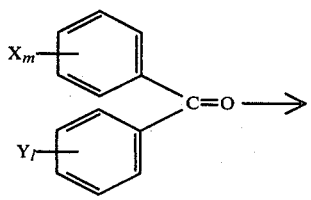

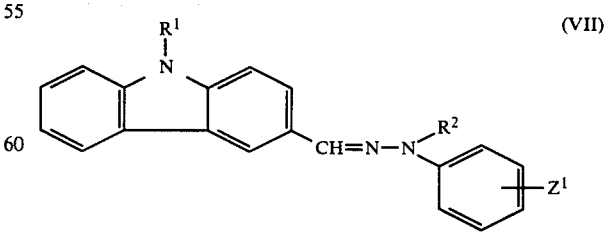

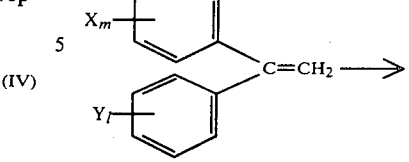

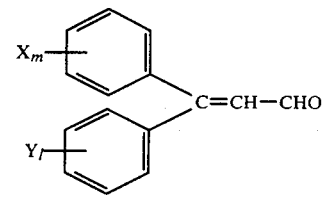

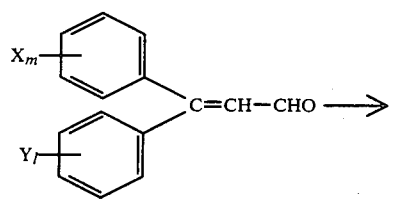

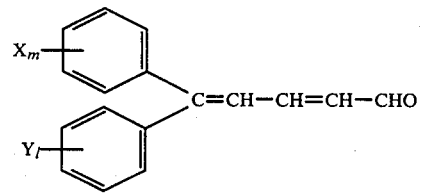

The electrophotographic plate according to this invention comprises a photosensitive layer containing one or more hydrazone compounds represented by the general formula (I).

The hydrazone compound represented by the general formula (I) exhibits extremely excellent performance as the organic semiconductor. Particularly, when used as a charge transport material, it provides a photosensitive plate particularly excellent in the sensitivity and the durability.

There may be contained in the photosensitive layer an additional charge transport material such as a hydrazone compound, pyrazoline compound or the like which acts as an electron-donating compound.

Representative of such charge transport materials are hydrazone compounds represented by the following general formula (VII):

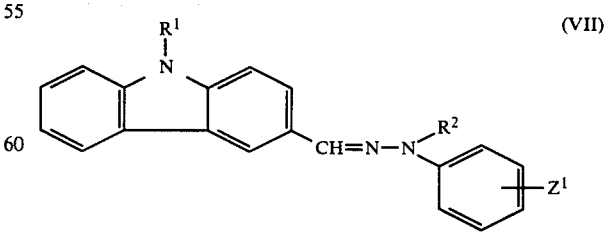  (VII)

(where $R^1$ represents an alkyl group, a substituted alkyl group or an aralkyl group, $R^2$ represents an alkyl group, a substituted alkyl group, allyl group, phenyl group, naphthyl group or an aralkyl group, and $Z^1$ represents hydrogen atom, an alkyl group, an alkoxy group or a halogen atom.)

The preferred compounds are those wherein $R^1$ is a lower alkyl group; $R^2$ is methyl, phenyl or naphthyl; and $Z^1$ is hydrogen atom in the above general formula (VII).

When the hydrazone compound of the general formula (I) is used in combination with that of the general formula (VII), the weight ratio of the former to the latter is preferably from 0.25 to 4.

While there have been various known forms for the photosensitive layer of the electrophotographic plate, the photosensitive layer in the electrophotographic plate according to this invention may be in any one of such forms. For instance, they include a photosensitive layer formed by adding a hydrazone compound and optionally, a dye serving as a sensitizer and an electron-attracting compound into a binder; a photosensitive layer formed by adding photoconductive particles which generate charge carriers at an extremely high efficiency upon absorption of light and a hydrazone compound into the binder; and a photosensitive layer prepared by laminating a charge transporting layer composed of the hydrazone compound and a binder with a charge generating layer composed of photoconductive particles which generate charge carriers at an extremely high efficiency upon absorption of light or those photoconductive particles and a binder.

In this invention, a photosensitive plate with particularly high sensitivity and low residual potential and further with excellent durability upon repeated use such as less fluctuation in the surface potential, less reduction in the sensitivity and less accumulation of the residual potential can be obtained in the case of using the hydrazone compound represented by the above general formula (I) as the charge transport layer in the photosensitive layer comprising two layers of the charge generating layer and the charge transport layer.

The electrophotographic plate according to this invention can be prepared in accordance with a conventional process, by dissolving a hydrazone compound represented by the above general formula (I) together with a binder into an appropriate solvent and adding, if required, photoconductive particles which generate charge carriers at an extremely high efficiency upon absorption light, a sensitizing dye, an electron-attracting compound or other additives such as a plasticizer and a dye to prepare a coating solution and applying and drying the same onto a conductive support to form a photosensitive layer usually of several tens micron in film thickness. In case of the photosensitive layer comprising two layers of the charge generating layer and the charge transport layer, it can be produced either by applying the coating solution referred to above on the charge generating layer or by forming a charge generating layer on the charge transport layer obtained by applying the coating solution.

The solvent for preparing the coating solution includes those solvents capable of dissolving the hydrazone compound, for example, ethers such as tetrahydrofuran, 1,4-dioxane and the like; ketones such as methylethyl ketone, cyclohexanone and the like; aromatic hydrocarbons such as toluene, xylene and the like; aprotic polar solvent such as N,N-dimethylformamide, acetonitrile, N-methylpyrrolidone, dimethylsulfoxide and the like; esters such as ethyl acetate, methyl formate, methyl cellosolve acetate and the like; and chlorinated hydrocarbons such as dichloroethane, chloroform and the like. It is, of course, necessary to select a solvent capable of also dissolving the binder among them. The binder includes various polymers which are compatible with the hydrazone, for example, polymers and copolymers of vinyl compounds such as styrene, vinyl acetate, vinyl chloride, acrylate, methacrylate, butadiene and the like; polyvinyl acetal, polycarbonate, polyester, polysulfone, polyphenyleneoxide, polyurethane, cellulose ester, cellulose ether, phenoxy resin, silicon resin, epoxy resin and the like. The amount of the binder employed is usually within a range of 0.5–30 times, and, preferably, 1–10 times the weight of the hydrazone.

For all of the photoconductive particles, the dye, and the electron-attracting compound to be added to said photosensitive layers, well-known materials can be used. The photoconductive particles generating charge carriers include inorganic photoconductive particles such as selenium, selenium-tellurium alloy, selenium-arsenic alloy and cadmium sulfide; and organic photoconductive particles such as copper phthalocyanine, perynone dyes, thioindigo, quinacridone, perylene dyes, anthraquinone dyes, azo dyes, bisazo dyes, cyanine dyes and the like. The dye includes, for instance, triphenylmethane dyes such as Methyl Violet, Brilliant Green, Crystal Violet, etc. thiazine dyes such as Methylene Blue and the like, quinone dyes such as Qunizalin and the like, cyanine dyes, pyrilium salts, thiapyrilium salts, benzopyrilium salts and the like. Further, the electron-attracting compound forming a charge transfer complex together with the hydrazone compound includes, for example, quinones such as chloranil, 2,3-dichloro-1,4-naphthoquinone, 2-methylanthraquinone, 1-nitroanthraquinone, 1-chloro-5-nitroanthraquione, 2-chloroanthraquinone, phenanthrenequinone and the like; aldehydes such as 4-nitrobenzaldehyde and the like; ketones such as 9-benzoylanthracene, indanedione, 3,5-dinitrobenzo-phenone, 2,4,7-trinitrofluorenone, 2,4,5,7-tetranitro-fluorenone, 3,3',5,5'-tetranitrobenzophenone and the like; acid anhydrides such as phthalic anhydride, 4-chloro-naphthalic anhydride and the like; cyano compounds such as tetraphthalal malononitrile, 4-nitrobenzal malononitrile and the like; and phthalides such as 3-benzalphthalide, 3-($\alpha$-cyano-p-nitrobenzal)phthalide, 3-($\alpha$-cyano-p-nitro-benzal)-4,5,6,7-tetrachlorophthalide and the like.

Further, the photosensitive layer of the electrophotographic plate according to this invention may be incorporated with well-known plasticizers for the improvement of the film-forming property, flexibility and mechanical strength. The plasticizers to be added into the coating solution as mentioned above include phthalic ester, phosphoric ester, epoxy compound, chlorinated paraffin, chlorinated fatty acid ester and aromatic compound such as methylnaphthalene and the like. In the case of using hydrazone compound as the charge transport material in the charge transport layer, although the coating solution may be of the composition as described above, the photoconductive particles, dye, electron-attracting compound and the like can be eliminated or added in a small amount. The charge generating layer in this case includes a thin layer prepared by vapor-depositing the photoconductive particles and, optionally, dye, electron-attracting compound and the like, and a thin layer prepared by coating a solution which is obtained by dissolving or dispersing the substances as mentioned above, optionally, with the binder or organic photoconductive materials into a solvent, and drying.

It will be apparent that the photosensitive plate thus formed may further comprise, as required, an adhesive layer, an intermediate layer and a transparent insulation layer as in commercially available electrophotographic photosensitive plates. Well-known materials employed for the electrophotographic photosensitive plates can be used as the electroconductive substrate on which the photosensitive layer is to be formed. Specifically, they include a drum or sheet of a metal such as aluminum and copper or a laminates of such material foils, or vapor-deposition products of such metals. They further include plastic film or paper electrified by coating an electroconductive substance such as metal powder, carbon black, copper iodide and high-molecular electrolytes together with an appropriate binder.

The electrophotographic photosensitive plate according to this invention has thus been explained specifically. The photosensitive plate according to this invention has an extremely high sensitivity and reduced residual potential causing foggings and, particularly, it has characteristic features of excellent durability due to its minimal light-fatigue showing less accumulation of the residual potential and less fluctuations in the surface potential and in the sensitivity during repeated use.

Having generally described the invention, a more complete understanding can be obtained by reference to certain examples which are provided herein for purposes of illustration only and are not intended to be limiting in any manner.

In the examples, "part" means "part by weight".

PREPARATION EXAMPLE

To a mixture of 57 g of triphenylphosphine and 100 ml of N,N-dimethylformamide, 31 g of methyl iodide was gradually added under the nitrogen stream. Stirring was continued for 2 hours while keeping the temperature of the solution at about 40° C. and, after adding 57 g of 4,4'-dimethoxybenzophenone, 42 g of sodium methylate solution (28% methanol) were added and refluxed for 3 hours. After the completion of the reaction, 130 ml of water was added to the cooled reaction solution and the mixture was stirred for one hour and then filtered to yield 34 g of the crystals.

Recrystallization from methanol-acetone mixture gave 27 g of α,α-bis(4-methoxyphenyl)ethylene (m. p. 138°–139° C.).

Then, 14 g of N-methylformanilide and 27 ml of phosphorus oxychloride were admixed and stirred at room temperature for 2 hours. To the thus obtained reaction solution, were gradually added 25 g of α,α-bis(4-methoxyphenyl)-ethylene and reacted at room temperature for 2 hours.

After the completion of the reaction, the reaction solution was cooled, to which 50 ml of saturated aqueous potassium acetate solution were dropped and, after stirring for 2 hours, extraction was effected using 500 ml of toluene.

Removing the toluene by distillation and separating the residue on a column chromatography, oily products with yellow-brown color were obtained. They were crystallized from methanol-hexane mixture to obtain 23 g of β,β-bis-(4-methoxyphenyl)acrolein (m. p. 54°–55° C.). 23 g of the β,β-bis(4-methoxyphenyl)acrolein and 19 g of N,N-diphenylhydrazine hydrochloride were suspended into 300 ml of methanol and the mixture was refluxed for 3 hours.

After the completion of the reaction, the products were cooled, deposited crystals were collected by filtration and purified through column chromatography to obtain 28 g of pale-yellow needle crystals of β,β-bis(4-methoxyphenyl)acrolein diphenylhydrazone (m.p. 132°–130° C.).

Other hydrazone compounds were prepared in accordance with the production process in this example.

EXAMPLE 1

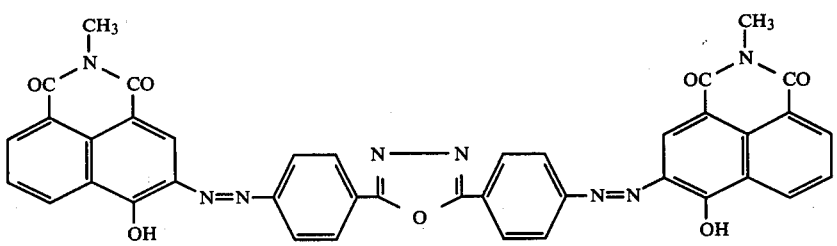

1.4 parts of a naphthalic acid type bisazo dye having the above structure and 2.7 g of phenoxy resin (manufactured by Union Carbide Corp. under the trade mark of PKHH) were dispersed into 100 g of cyclohexanone and they are finely pulverized by using a sand grinder. The liquid dispersion containing the fine particles were coated on an aluminumvapor deposition layer deposited on a polyester film of 75μ in thickness so as to provide a 0.3 g/m² dry weight by using a wire bar and, thereafter, dried to form a charge generating layer.

Onto the layer thus formed, was coated a solution containing 80 parts of β,β-diphenylacrolein diphenylhydrazone (m. p. 121°–122° C.) represented by the following structural formula:

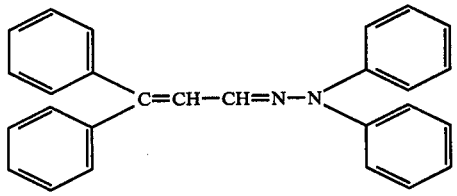

and 100 parts of polyester (manufactured by Toyobo Co., Ltd. under the trade mark of Vylon 85) dissolved in 570 parts of toluene, so as to provide a 13μ film thickness after the drying by using a film applicator and dried to form a charge transport layer.

The electrophotographic plate comprising the dual-layered photosensitive layer thus obtained exhibited, when measured, 5.9 lux.sec of sensitivity, that is, half-decay exposure intensity ($E_{\frac{1}{2}}$).

The half-decay exposure intensity was determined by at first charging the photosensitive plate in a dark place with corona discharge at −5.5 KV, then applying exposure with incandescent light and by measuring the exposure intensity required till the surface potential decayed to one-half of the initial surface potential.

EXAMPLE 2

A photosensitive plate was produced in the same manner as in Example 1 with the exception of the use of a naphthalic acid type bisazo dye represented by the following structural formula:

EXAMPLE 5

A charge transporting layer was formed onto a charge generating layer as prepared in Example 1 in the same manner as in Example 1 with the exception that β,β-bis-(4-methoxyphenyl)acrolein diphenylhydrazone (m. p. 132°-133° C.) represented by the following structural formula:

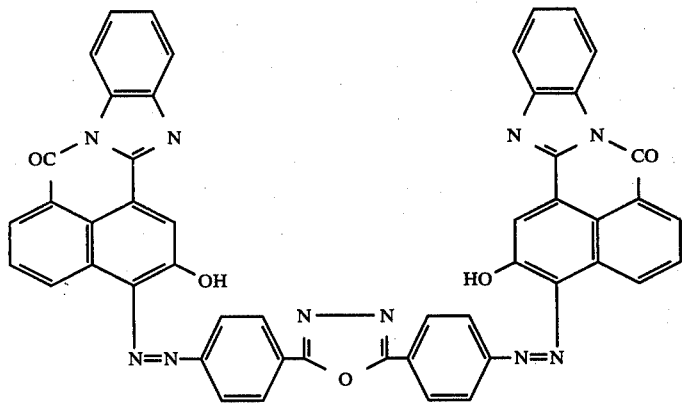

instead of the dye employed in Example 1.

$E_{\frac{1}{2}}$ was 3.2 lux.sec when measured in the same manner as in Example 1.

$E_{\frac{1}{2}}$ after repeating 2000 cycles of charge and exposure was 3.6 lux.sec showing extremely less fluctuation in the sensitivity.

EXAMPLE 3

A solution containing 80 parts of β-(4-methoxyphenyl)-β-phenylacrolein diphenylhydrazone (m. p. 166°-167° C.) represented by the following structural formula:

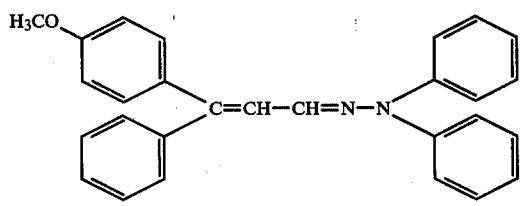

and 100 parts of polycarbonate (manufactured by Mitsubishi Chemical Industries Ltd. under the trade mark of NOVAREX 7025A) dissolved in 900 parts of dichloromethane was coated onto a charge generating layer used in Example 1 so as to provide a 13μ of film thickness after drying by using a film applicator and dried to form a charge transport layer.

$E_{\frac{1}{2}}$ was 7.7 lux.sec when measured in the same manner as in Example 1.

EXAMPLE 4

The photosensitive plate was prepared by using the dye used in Example 2, instead of the dye employed in Example 3, as a charge generating layer and coating thereover a charge transport layer employed in Example 3. This photosensitive plate had a half-decay exposure intensity of 2.8 lux.sec.

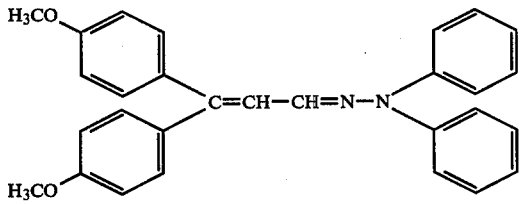

was used instead of β,β-diphenylacrolein diphenylhydrazone, and the photosensitive plate thus obtained had a half-decay exposure intensity of 4.7 lux.sec when measured.

While the photosensitive plate in this example exhibited an initial charging voltage of −552 V and a residual potential of −10 V, its properties remained stable even after 2000 cycles of charge and exposure having the charging voltage of −536 V and the residual potential of −32 V, the fluctuation in the sensitivity being extremely small.

Furthermore, this photosensitive plate exhibited a low residual potential of −21 V after applying exposure with 500 lux incandescent light for 5 minutes and repeating 500 cycles of charge and exposure.

An initial charging voltage was 96% of the charging voltage before exposure. There was not observed a big increase in the residual potential as well as a big decrease in the charge voltage each caused by the light-fatigue.

The photosensitive plate of this invention has low light-fatigue and is stable to repeated use. Therefore, it has excellent durability.

EXAMPLE 6

A photosensitive plate prepared by coating the charge transport layer produced in Example 5 on the charge generating layer produced in Example 2 exhibited the half-decay exposure intensity of 3.2 lux.sec.

EXAMPLE 7

A charge transport layer was coated in the same manner as in Example 1 onto the charge generating layer produced in Example 1 except that β,β-ditolylacrolein diphenyl-hydrazone (m. p. 152°–154° C.) represented by the following structural formula:

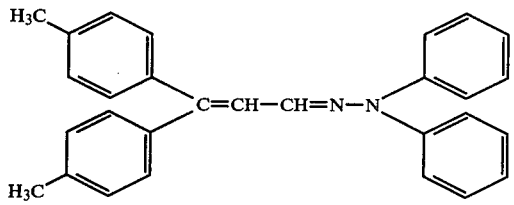

was used instead of β,β-diphenylacrolein diphenylhydrazone, and the photosensitive plate thus obtained exhibited the half-decay exposure intensity of 5.7 lux.-sec.

EXAMPLE 8

A charge transport layer was coated in the same manner as in Example 1 onto the charge generating layer produced in Example 1 except that a diphenylhydrazone (m. p. 131°–132° C.) represented by the following structural formula:

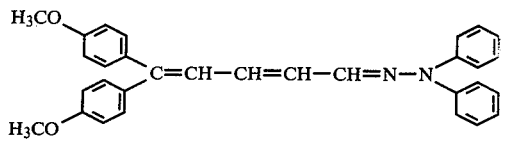

was used instead of β,β-diphenylacrolein diphenylhydrazone, and the photosensitive plate thus obtained exhibited the half-decay exposure intensity, when measured, of 4.8 lux.sec.

EXAMPLE 9

Charge transport layers (9-1–9-4) each containing a hydrazone compound shown in Table 1 below instead of β,β-diphenylacrolein diphenylhydrazone were provided on the charge generating layer produced in Example 1 to prepare photosensitive plates and the half-decay exposure intensities ($E_{\frac{1}{2}}$) thereof were measured to obtain the results as shown in Table 1.

TABLE 1

| Example | Hydrazone compound in charge transporting layer | $E_{\frac{1}{2}}$ (lux.sec) |
| --- | --- | --- |
| 9-1 | [structure] | 5.8 |
| 9-2 | [structure] | 5.2 |
| 9-3 | [structure] | 5.4 |
| 9-4 | [structure] | 5.9 |

EXAMPLE 10

A solution of 45 parts of β,β-bis(4-methoxyphenyl)acrolein diphenylhydrazone, 45 parts of N-ethylcarbazole-3-carbaldehyde diphenylhydrazone and 100 parts of methacrylic resin (manufactured by Mitsubishi Rayon Company, Ltd.) in 570 parts of toluene was

What is claimed is:

1. An electrophotographic plate, comprising:
a photosensitive layer containing a hydrazone compound of formula (I):

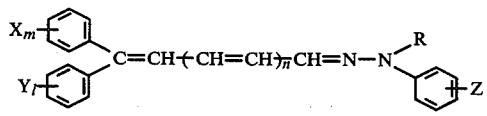

(I)

wherein X, Y and Z are each independently hydrogen, a lower alkyl group, a lower alkoxy group, phenoxy or an arylalkoxy group; R is hydrogen, a lower alkyl group, allyl, an aralkyl group or a substituted or unsubstituted phenyl group; m and l are each independently 1 or 2; and n is 0 or 1 in a binder laminated with a charge generating layer which is binderless photoconductive particles or photoconductive particles in a binder.

2. The electrophotographic plate of claim 1, wherein the photoconductive particles in said charge generating layer are inorganic particles selected from the group consisting of selenium, selenium-tellurium alloy, selenium-arsenic alloy and cadmium sulfide or organic particles selected from the group consisting of copper phthalocyanine, perynone dyes, thioindigo, quinacridone, perylene dyes, anthraquinone dyes, azo dyes, bisazo dyes, and cyanine dyes.

3. An electrophotographic plate, comprising:
a photosensitive layer containing a hydrazone compound of formula (I):

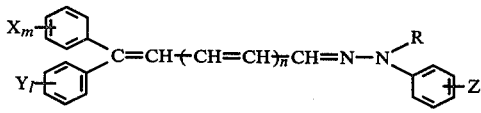

(I)

wherein X, Y and Z are each independently hydrogen, a lower alkyl group, a lower alkoxy group, phenoxy or an arylalkoxy group; R is hydrogen, a lower alkyl group, an allyl group, an aralkyl group or a substituted or unsubstituted phenyl group; m and l are each independently 1 or 2; and n is 0 or 1 in a binder.

4. The electrophotographic plate of claim 3, wherein said photosensitive layer further comprises a sensitizing compound and an electron-attracting compound.

5. The electrophotographic plate of claim 4, wherein said sensitizing compounds is a dye selected from the group consisting of triphenylmethane dyes, thiazine dyes, quinone dyes, cyanine dyes, pyrilium salts, thiapyrillium salts, and benzopyrilium salts.

6. The electrophotographic plate of claim 4, wherein said electron-attracting compound is a quinone, an aldehyde, a ketone, an acid anhydride, a cyano compound or a phthalide.

7. An electrophotographic plate, comprising:
a photosensitive layer containing a hydrazone compound of formula (I):

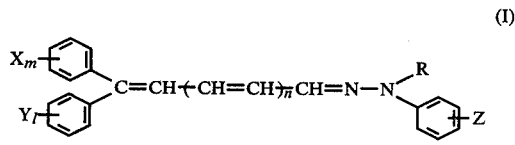

(I)

wherein X, Y and Z are each independently hydrogen, a lower alkyl group, a lower alkoxy group, phenoxy or an arylalkoxy group; R is hydrogen, a lower alkyl group, allyl, an aralkyl group or a substituted or unsubstituted phenyl group; m and l are each independently 1 or 2; and n is 0 or 1 and photoconductive particles which generate charged carriers in a binder.

8. The electrophotographic plate of claim 7, wherein said photoconductive particles are inorganic particles selected from the group consisting of selenium, selenium-tellurium alloy, selenium-arsenic alloy and cadmium sulfide; or organic particles selected from the group consisting of copper phthalocyanine, perynone dyes, thioindigo, quinacridone, perylene dyes, anthraquinone dyes, azo dyes, bisazo dyes, and cyanine dyes.

9. The electrophotographic plate of claim 3, 7 or 1, wherein X, Y and Z are each independently hydrogen, a lower alkyl group or a lower alkoxy group; R is a lower alkyl group, phenyl or an aralkyl group; m and l are each 1 and n is 0 or 1.

10. The electrophotographic plate of claim 9, wherein X and Y are each a lower alkoxy group, Z is hydrogen and R is phenyl.

11. The electrophotographic plate of claim 3, 7 or 1, wherein said photosensitive layer additionally contains a hydrazone compound of the formula (VII):

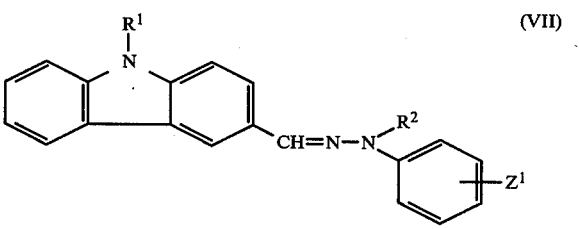

(VII)

wherein $R^1$ is an alkyl group, a substituted alkyl group or an aralkyl group; $R^2$ is an alkyl group, a substituted alkyl group, allyl, phenyl, naphthyl or an aralkyl group; and $Z^1$ is hydrogen, an alkyl group, an alkoxy group or a halogen atom.

12. The electrophotographic plate of claim 11, wherein $R^1$ is a lower alkyl group, $R^2$ is methyl, phenyl or naphthyl and $Z^1$ is hydrogen.

13. The electrophotographic plate of claim 11, wherein the weight ratio of the hydrazone compound of formula (I) to the hydrazone compound of formula (VII) is from 0.25 to 4.

* * * * *